US006573717B2

(12) United States Patent
Thesen

(10) Patent No.: US 6,573,717 B2
(45) Date of Patent: Jun. 3, 2003

(54) METHOD FOR THE OPERATION OF A MAGNETIC RESONANCE APPARATUS

(75) Inventor: Stefan Thesen, Meckenheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/922,505

(22) Filed: Aug. 3, 2001

(65) Prior Publication Data

US 2002/0036499 A1 Mar. 28, 2002

(30) Foreign Application Priority Data

Aug. 8, 2000 (DE) ........................................ 100 38 669

(51) Int. Cl.[7] .................................................. G01V 3/00
(52) U.S. Cl. ...................................................... 324/307
(58) Field of Search ................................ 324/309, 307, 324/318, 322

(56) References Cited

U.S. PATENT DOCUMENTS 4,780,675 A * 10/1988 DeMeester et al. ......... 324/312
4,851,779 A * 7/1989 DeMeester et al. ......... 324/312
5,043,665 A 8/1991 Kuhara et al.
5,218,299 A * 6/1993 Dunkel ....................... 324/307
5,233,302 A * 8/1993 Xiang et al. ................ 324/307
5,325,060 A * 6/1994 Mansfield et al. .......... 324/322
5,379,766 A 1/1995 McKinnon et al.
5,833,609 A * 11/1998 Dannels et al. ............. 324/306
5,933,006 A 8/1999 Rasche et al.
5,977,769 A 11/1999 Börnert et al.
6,067,465 A * 5/2000 Foo et al. ................... 324/309
6,157,677 A * 12/2000 Martens et al. .......... 348/416.1
6,242,916 B1 * 6/2001 King .......................... 324/309
6,307,369 B1 * 10/2001 Felmlee et al. ............. 324/307
6,341,179 B1 * 1/2002 Stoyle et al. ............... 382/254
6,369,568 B1 * 4/2002 Ma et al. .................... 324/307

FOREIGN PATENT DOCUMENTS

DE 198 60 038 6/2000

OTHER PUBLICATIONS

"Real Time Head Motion Correction for Functional MRI," Eviatar et al., Proc. of ISMRM 7 (1999), p. 269.
"Correction of Motional Artifacts in Diffusion–Weighted MR Images Using Navigator Echoes," Ordidge et al., Magnetic Resonance Imaging, vol. 12, No. 3, (1994), pp. 445–460.

* cited by examiner

*Primary Examiner*—Edward Lefkowitz
*Assistant Examiner*—Dixomara Vargas
(74) *Attorney, Agent, or Firm*—Schiff Hardin & Waite

(57) ABSTRACT

In a method for the operation of a magnetic resonance apparatus, nuclear magnetic signals obtained from an image region of an examination subject that is positioned in an imaging volume of the apparatus are entered into a k-space matrix as respective complex numbers are a motion model is determined with which translational motion of the subject with respect to the imaging volume can be described with a time-dependency, at least for prescribable points of the image region. The motion model is determined with respective phase values of at least two values of the k-space matrix that are point-symmetrically located in the k-space matrix with respect to a symmetry point of the k-space matrix. These two values behave as complex conjugates of each other in the absence of any motion between the registration times of the two values, and, any translational motion is thus reflected in the phase values. The values of the k-space matrix are corrected according to the motion model determined in this manner.

10 Claims, 3 Drawing Sheets

METHOD FOR THE OPERATION OF A MAGNETIC RESONANCE APPARATUS

BACKGROUND OF THE INVENTION

1. Field of the Invention

The present invention is directed to a method for the operation of a magnetic resonance apparatus.

2. Description of the Prior Art

Magnetic resonance technology is a known technique for generating images of a body interior of an examination subject. To that end, rapidly switched gradient fields are superimposed on a static, basic magnetic field in a magnetic resonance apparatus. Further, radio-frequency signals are radiated into the examination subject for triggering magnetic resonance signals. The resulting magnetic resonance signals are registered and image datasets and magnetic resonance images are produced on the basis thereof. The magnetic resonance signals are deleted (received) by a radio-frequency system, demodulated in phase-sensitive fashion and converted into values respectively represented as complex numbers by sampling and analog-to-digital conversion. These values are entered into a k-space matrix forming an image dataset. Using a multi-dimensional Fourier transformation, an appertaining magnetic resonance image can be reconstructed from the k-space matrix occupied with these values.

In a known method for magnetic resonance imaging, at least one-half of the locations in the k-space matrix is occupied with values that, as described above, are acquired directly from magnetic resonance signals. The other half of the locations is occupied with values that are respectively calculated from the aforementioned values by complex conjugation. It is thereby assumed that the respective values of two locations of the k-space matrix that are point-symmetrically arranged with respect to a symmetry point of the k-space matrix, generally a selected zero point, behave in conjugate complex fashion relative to one another. Methods of this type are known as half-Fourier techniques and are disclosed in greater detail in, for example, U.S. Pat. No. 5,043,665.

Without countermeasures, positional changes of a region of the examination subject relative to the magnetic resonance apparatus during an overall time span of the registration of the k-space matrix lead to unwanted distortions of the magnetic resonance image. Such positional changes can arise, for example, due to movement of the examination subject, for example a patient.

The article by H. Eviatar et al., "Real Time Head Motion Correction for Functional MRI", Proc. of ISMRM 7 (1999), page 269 discloses a method wherein positional changes of a patient's head during the overall registration time of an image dataset are acquired in the framework of a functional magnetic resonance imaging, and wherein an acquired positional change is taken into consideration during the further registration of the image dataset. To this end, the magnetic resonance apparatus has an optical acquisition system with which optical reflectors attached to the patient's head can be monitored as to their position.

Further, positional changes of the region to be imaged during a registration of diffusion magnetic resonance images are especially critical. For producing a diffusion image, at least one first image dataset and one second image dataset of the region to be imaged are registered, the first being registered, for example, with a sequence having diffusion-emphasizing gradient pulse with high strength and a long duration, and the second being registered without the aforementioned gradient pulses. The diffusion image derives from a corresponding subtraction of the two image datasets in the display thereof. In particular, positional changes of the imaged region during the registration of the diffusion-emphasizing image dataset lead to serious misinformation with respect to the diffusion to be actually acquired. An identification of positional changes is therefore implemented when registering the diffusion-emphasizing image dataset with a sequence that has a number of radio-frequency excitation pulses with temporally intervening acquisition phases. Effects of positional changes that are identified are thereby correspondingly corrected. Similar to navigator echo technique, a so-called correction echo is generated and registered at every radio-frequency excitation and is compared to a reference correction echo for acquiring the positional change. Further details of this approach are described, for example, in the article by R. J. Ordidge et al., "Correction of Motional Artifacts in Diffusion Weighted MR-images Using Navigator Echos", Magnetic Resonance in Medicine (12), 1994, pages 455–460. The overall registration time of the diffusion image is lengthened due to the correction echos.

SUMMARY OF THE INVENTION

An object of the present invention is to provide a method for the operation of a magnetic resonance apparatus with which positional changes of an imaged region during an overall registration time of a k-space matrix can be determined in a simple and time-efficient way, so that image artifacts arising therefrom can be correspondingly corrected.

This object is inventively achieved in a method for the operation of a magnetic resonance apparatus wherein nuclear magnetic resonance signals obtained from an image region of an examination subject that is positioned in an imaging volume of the apparatus are entered into a k-space matrix as respective complex numbers are a motion model is determined with which translational motion of the subject with respect to the imaging volume can be described with a time-dependency, at least for prescribable points of the image region. The motion model is determined with respective phase values of at least two values of the k-space matrix that are point-symmetrically located in the k-space matrix with respect to a symmetry point of the k-space matrix. These two values behave as complex conjugates of each other in the absence of any motion between the registration times of the two values, and, any translational motion is thus reflected in the phase values. The values of the k-space matrix are corrected according to the motion model determined in this manner.

As a result, motion of the examination subject which occurs during registration of an image dataset can be identified and the effects thereof on the magnetic resonance image can be corrected without correction or navigator echos that lengthen the exposure time having to be registered for this purpose, and without having to provide any kind of additional motion acquisition devices, such as optical devices.

The inventive method is not limited to k-space matrices that are completely occupied with values acquired from magnetic resonance signals. The method can likewise be applied to k-space matrices wherein only a little more than a half of the matrix locations are occupied with values acquired from magnetic resonance signals. The method thus also can be employed in the half-Fourier techniques wherein generally more than half of the values are directly acquired. The acquired values, exceeding half of the matrix locations, are correspondingly utilized for determining the motion model.

An especially advantageous employment of the method is for a magnetic resonance image exposure of shoulders of a patient. As experience has shown, it is difficult for the patient to keep the shoulders still for several minutes in a designated fixed position required for the exposure.

In a preferred development, the time-dependency of the translational motion is described by registration times for values of the k-space matrix. Given knowledge of the registration times of all values of an image dataset, any translational motion can be identified and correspondingly corrected regardless of whether it occurs during an acquisition phase for magnetic resonance signals or in preparation phases between the acquisition phases.

In another embodiment, motion between registration times of values that are to be allocated to a single radio-frequency excitation is left out of consideration. The determination of the motion model thus is correspondingly simplified. This is particularly meaningful given sequences wherein longer preparation phases occur between short acquisition phases for the registration of the k-space matrix wherein magnetic resonance signals are acquired. Such preparation phases are required for the preparation of a spin ensemble in order to prepare corresponding magnetic resonance signals. This is typical of spin echo sequences.

In a further embodiment, the registration of, for example, the values for filling the k-space matrix is implemented with a slice technique. The resulting k-space matrix thus is two-dimensionally formed. The k-space matrix can then be considered a k-plane with a symmetry point. The same applies to the individual slices of a three-dimensional image dataset for which values are registered with a multi-slice technique. In multi-slice technique, a three-dimensional image dataset is generated that contains a number of two-dimensional k-space matrices.

In another embodiment, the registration of the values for filling the k-space matrix occupied is implemented with a volume technique. In contrast to the slice technique, a slice selection gradient is replaced by an additional phase coding gradient in the volume technique, so that a three-dimensional k-space matrix is registered.

DESCRIPTION OF THE PREFERRED EMBODIMENTS

Figure 1:
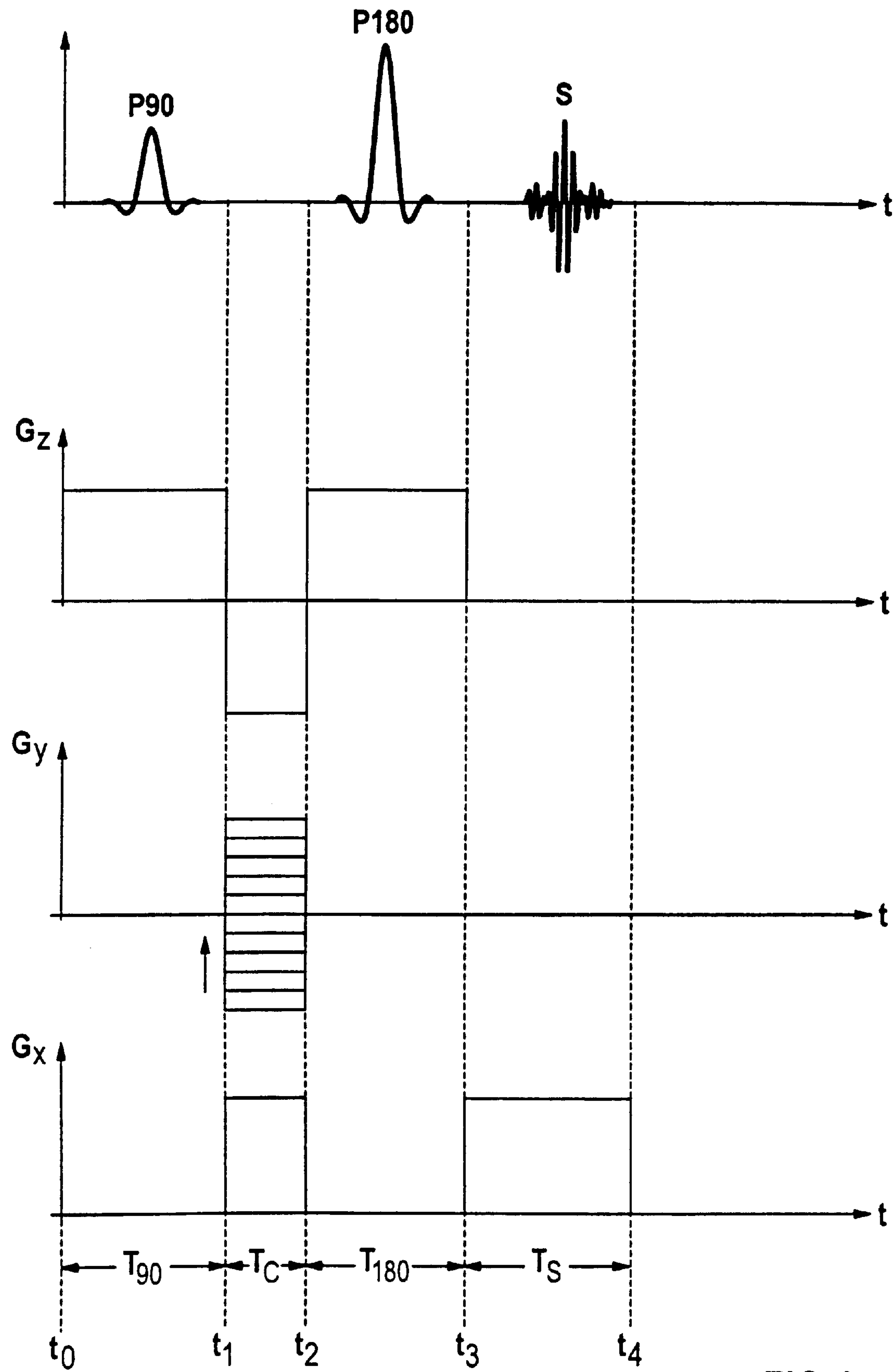
FIG. 1 illustrates a pulse and gradient series of a spin echo sequence.

FIG. 1 shows a pulse and gradient series of an embodiment of a spin echo sequence. The spin echo sequence begins with a time $t_0$ with a 90° radio-frequency excitation pulse P90 that is radiated into an examination subject during a time duration $T_{90}$ between the times $t_0$ and $t_1$. At the same time, a slice selection gradient $G_z$ is activated during the time duration $T_{90}$ that is directed in the z-direction of a Cartesian coordinate system. As a result of the 90° radio-frequency excitation pulse P90 and the slice selection gradient $G_z$, a region to be imaged within the examination subject is selectively excited as a slice during the time duration $T_{90}$.

In a time duration $T_c$ between the times $t_1$ and $t_2$ following the time duration $T_{90}$, the slice selection gradient $G_z$ is activated so that it acts in the opposite direction compared to the slice selection gradient $G_z$ during the time duration $T_{90}$, and has a gradient-time area that is equal to half the gradient-time area during the time duration $T_{90}$. As a result, unwanted dephasing effects during the slice-selective excitation are compensated to a good approximation. During the time $T_c$ and for location coding within the excited slice, further, a phase coding gradient $G_y$ is the y-direction of the Cartesian coordinate system and a readout gradient $G_x$ is activated in the x-direction of the Cartesian coordinate system.

In a time duration $T_{180}$ between the times $t_2$ and $t_3$ following the time duration $T_c$, a 180° radio-frequency pulse P180 is radiated into the examination subject for generating a spin echo signal. At the same time, the slice selection gradient $G_z$ is activated.

In a time duration $T_s$ following the time duration $T_{180}$, the spin echo signal S is phase-sensitively demodulated, sampled under the readout gradient $G_x$, and the complex-number values of the sampling points are stored in a k-space matrix.

Figure 2:
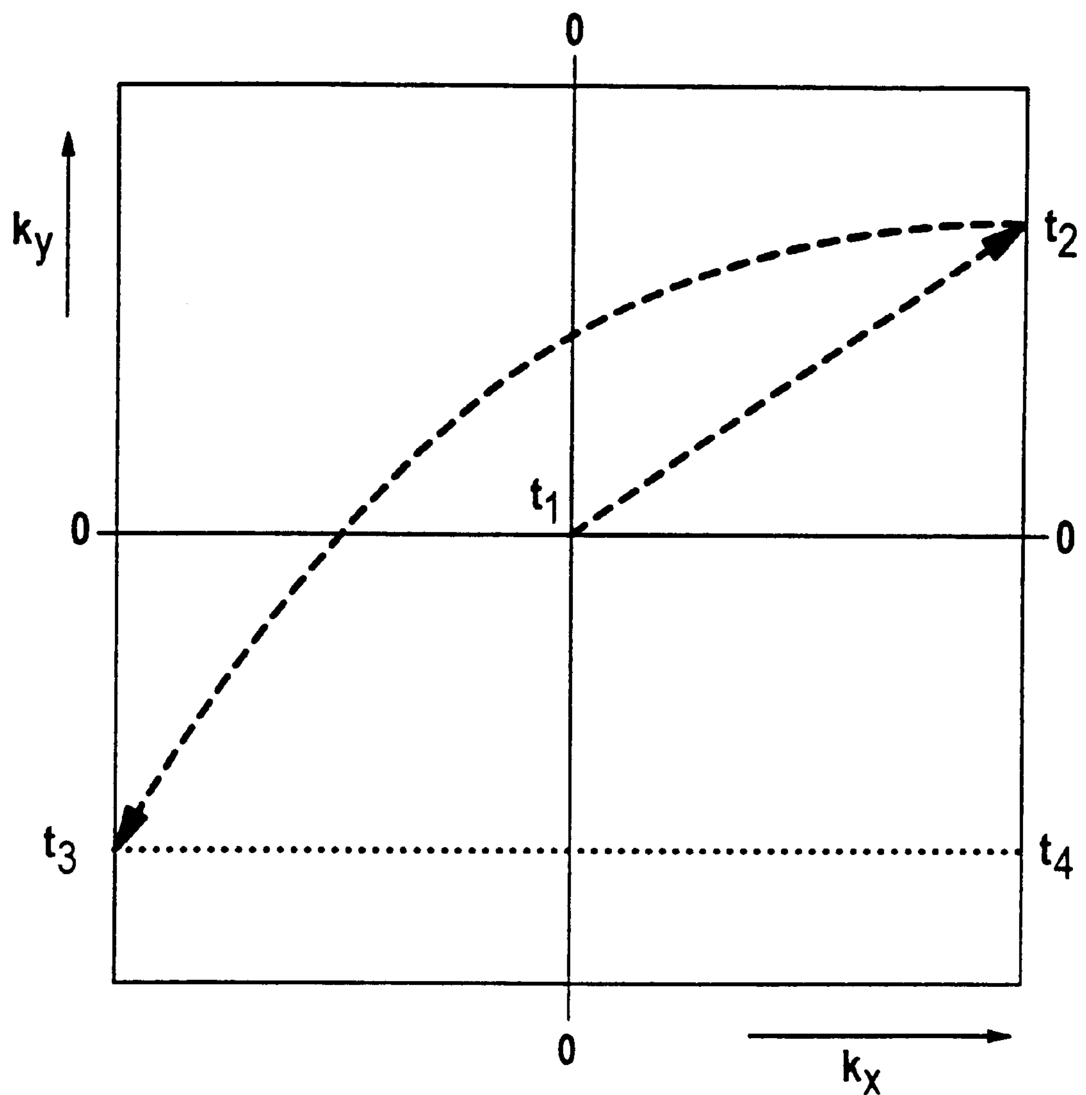
FIG. 2 illustrates a k-space occupied by values obtained using the spin echo sequence of FIG. 1.

Corresponding to the spin echo sequence shown in FIG. 1, FIG. 2 shows the appertaining k-space matrix, which is a two-dimensional k-space matrix in the described case of a slice-selective excitation. The following definition thereby applies for the k-space:

$$k_x(t) = \gamma \int_0^t G_x(t')\,dt',\ k_y(t) = \gamma \int_0^t G_y(t')\,dt' \text{ and } k_z(t) = \gamma \int_o^t G_z(t')\,dt'.$$

wherein $\gamma$ is thereby the Larmor constant. A magnetic resonance image can be reconstructed from the k-space matrix occupied with such values since a mathematical relationship exists between the image space and the k-space via a multi-dimensional Fourier transformation. FIG. 2 also shows the path along which the k-plane is traversed according to the sequence illustrated in FIG. 1. During the time duration $T_{90}$ one is at the zero point of the k-plane, which is the symmetry point at the same time. After the end of the time duration $T_c$, one is located at a k-space point at the right edge of the k-plane. Via the aforementioned equations, the coordinates $k_x$ and $k_y$ of the respective k-space points are determined by the time duration $T_c$ as well as a amplitude of the phase coding gradient $G_x$ or $G_y$ during the time duration $T_c$. During the time duration $T_{180}$, this k-space point is mirrored at the zero point of the k-plane due to the 180° radio-frequency pulse P180. Proceeding from the mirrored k-space point, a row of the k-space matrix is traversed in $k_x$-direction during the time duration $T_s$. Samples of the spin echo signal S are thereby correspondingly entered (stored) in the k-space matrix in equidistant steps between the times $t_3$ and $t_4$. Each of the samples has a magnitude and a phase as a complex number. For a complete filling of the k-space matrix, the spin echo sequence of FIG. 1 is repeated with different intensities of the phase coding gradient $G_y$ in conformity with a given number of rows of the k-space matrix to be occupied.

The values of the k-space matrix that are point-symmetrically located relative to one another with respect to the zero point of the k-space are complex conjugates of one another if the examination subject was immobile during the implementation of the sequence and exhibited no internal flow phenomena. This means they have an identical magnitude and phase, that only differ in terms of operational sign. Thus, $f(k_x, k_y)=f^*(-k_x, -k_y)$ applies for values $f(k_x, k_y)$ of two matrix elements that are point-symmetrically arranged relative to one another. The above-described symmetry property is disturbed (altered) by movement of the examination subject during the implementation of a sequence. Translational movements of the examination subject in at least one of the directions of the Cartesian coordinate system lead to phase values that are no longer equal for entries that are point-symmetrically located relative to one another in the matrix.

The inventive method described in an example below on the basis of the flowchart of FIG. 3 makes use of the aforementioned property. Without limitation as to its universality, the method is explained based on the sequence shown in FIGS. 1 and 2.

Further simplifying assumptions that do not represent a limitation as to the universality of the method also made during the course of the explanation for clarity and a simple presentation.

Figure 3:
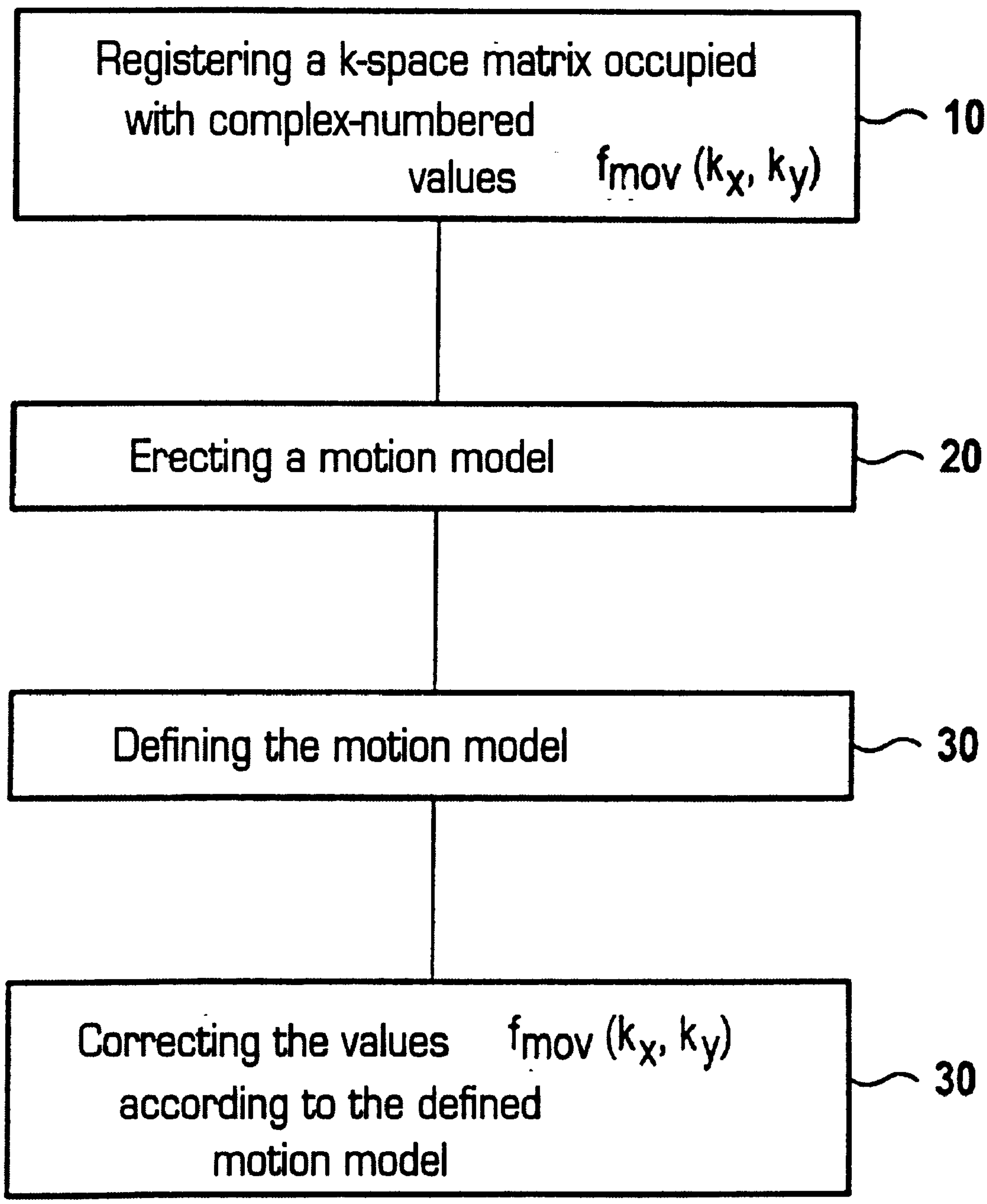
FIG. 3 is a flowchart of an exemplary embodiment of the invention.

In a first step 10 of the flowchart of FIG. 3, a k-space matrix is filled so as to be occupied with complex-number values $f_{mov}(k_x, k_y)$. A positional change of the region to be imaged can occur between the registration times of two different values $f_{mov}(k_x, k_y)$. Corresponding to that set forth with respect to FIG. 2, the occupation of the k-space matrix with the values $f_{mov}(k_x, k_y)$ ensues row-by-row by repeating the sequence shown in FIG. 1 with different amplitudes of the phase coding gradient $G_y$. The entire operation for filling the k-space matrix for generating a two-dimensional magnetic resonance image lasts several seconds or even minutes. In contrast thereto, the time durations $T_s$ wherein the spin echo signals S are sampled and the actual filling of the k-space matrix occurs only amount to a few milliseconds.

Proceeding from the latter fact, a movement by the examination subject, a positional change of the region to be imaged, to be more precise, during the time durations $T_s$ is left out of consideration in a good approximation for simplifying the rest of the presentation. For further simplification of the rest of the presentation, it is assumed that the phase coding gradient $G_y$ is switched proceeding from a minimum amplitude up to a maximum amplitude in the repetitions of the sequence. A proportionality of the k-space coordinate $k_y$ to the time t thus is obtained.

A motion model is erected in a step 20 of the flowchart of FIG. 3 following the step 10. For simplicity, a two-dimensional, linear translational movement of the imaged region in the x-direction and the y-direction with a time dependency that is described by the k-space coordinate $k_y$ thereby forms the basis. In the image space, the translational motion for the x-direction thus can be described by $\Delta x$ and that for the y-direction can be described by $\Delta y$ within the framework of the following motion model $$\Delta x=k_y\cdot\Delta I_x$$

$$\Delta y=k_y\cdot\Delta I_y$$

The unknown $\Delta l_x$ is the shift in the x-direction that occurs from one amplitude of the phase coding gradient $G_y$ to the next amplitude of the phase coding gradient $G_y$. The analogous case applies for the unknown $\Delta I_y$ in the y-direction.

The motion model, the unknowns $\Delta I_x$ and $\Delta I_y$ thereof to be more precise, are determined in a step 30 of the flowchart of FIG. 3 that follows the step 20. As is known, picture elements $\tilde{f}(x, y)$ of the image space are linked (related) via a two-dimensional Fourier transformation to values $f(k_x, k_y)$ of k-space:

$$\tilde{f}(x, y) = \frac{1}{N^2}\sum_{k_x,k_y}\left|f(k_x, k_y)\right|\cdot e^{\frac{2\pi i}{N}(k_x\cdot x+k_y\cdot y)} = \frac{1}{N^2}\sum_{k_x,k_y} f(k_x, k_y)$$

In FIG. 2, N represents a number of samples that are acquired upon traversal of a k-space row, this number N being equal to the number of rows traversed overall for simplicity.

According to the shifting property of the Fourier transform, the linear motion in the image space causes a corresponding auxiliary phase in k-space:

$$\begin{aligned}\tilde{f}(x+\Delta x, y+\Delta y) &= \frac{1}{N^2}\sum_{k_x,k_y} f(k_x, k_y)\cdot e^{\frac{2\pi i}{N}\cdot k_x\cdot\Delta x}\cdot e^{\frac{2\pi i}{N}\cdot k_y\cdot\Delta y}\\ &= \frac{1}{N^2}\sum_{k_x,k_y} f_{mov}(k_x, k_y)\end{aligned}$$

The following is thus valid for a value $f_{mov}(k_x, k_y)$ in the motional case compared to a corresponding value $f(k_x, k_y)$ in the immobile case:

$$f_{mov}(k_x, k_y) = f(k_x, k_y)\cdot e^{\frac{2\pi i}{N}\cdot k_x\cdot\Delta x}\cdot e^{\frac{2\pi i}{N}\cdot k_y\cdot\Delta y}$$

The following is obtained by inserting the linear motion model for $\Delta x$ and $\Delta y$:

$$f_{mov}(k_x, k_y) = f(k_x, k_y)\cdot e^{\frac{2\pi i}{N}\cdot k_x\cdot k_y\cdot\Delta 1_x}\cdot e^{\frac{2\pi i}{N}\cdot k_y^2\cdot\Delta 1_y}$$

A multiplication of two values $f_{mov}(k_x, k_y)$ that are arranged point-symmetrically relative to one another in the k-space matrix of the motional case yields:

$$\begin{aligned}&f_{mov}(+k_x, +k_y)\cdot f_{mov}(-k_x, -k_y) =\\ &f(k_x, k_y)\cdot e^{\frac{2\pi i}{N}\cdot k_x\cdot k_y\cdot\Delta 1_x}\cdot e^{\frac{2\pi i}{N}\cdot k_y^2\cdot\Delta 1_y}\cdot f(-k_x, -k_y)\cdot e^{\frac{2\pi i}{N}\cdot(-k_x)\cdot(-k_y)\cdot\Delta 1_x}\cdot\\ &e^{\frac{2\pi i}{N}\cdot(-k_y)^2\cdot\Delta 1_y} = f(k_x, k_y)\cdot f^*(k_x, k_y)\cdot e^{\frac{4\pi i}{N}\cdot k_x\cdot k_y\cdot\Delta 1_x}\cdot e^{\frac{4\pi i}{N}\cdot k_y^2\cdot\Delta 1_y} =\\ &|f(k_x, k_y)|^2\cdot e^{\frac{4\pi i}{N}\cdot(k_x\cdot k_y\cdot\Delta 1_x+k_y^2\cdot\Delta 1_y)}\end{aligned}$$

Due to the equality of the magnitudes $$|f(k_x, k_y)|^2=|f_{mov}(+k_x,+k_y)\cdot f_{mov}(-k_x, -k_y)|^2$$

the following thus derives:

$$\frac{f_{mov}(+k_x, +k_y)\cdot f_{mov}(-k_x, -k_y)}{|f_{mov}(+k_x, +k_y)\cdot f_{mov}(-k_x, -k_y)|^2} = e^{\frac{4\pi i}{N}\cdot(k_x\cdot k_y\cdot\Delta 1_x+k_y^2\cdot\Delta 1_y)}$$

In the immobile case, the latter equation yields one, and yields a phase value deviating from zero in the case of movement. The two unknowns $\Delta I_x$ and $\Delta I_y$ of the motion model can be defined by at least two value pairs whose values $f_{mov}(k_x, k_y)$ are arranged point-symmetrically relative to one another in the k-space matrix. When a number of values $f_{mov}(k_x, k_y)$ up to all values $f_{mov}(k_x, k_y)$ are involved, then the two unknowns $\Delta I_x$ and $\Delta I_y$ can be estimated in stable fashion by a fit method that minimizes the square of the error.

In a step 40 of the flowchart of FIG. 3 following the step 30, the values $f_{mov}(k_x, k_y)$ of the k-space matrix are corrected corresponding to the defined motion model. Use of the following equation is made for determining the corrected values $f(k_x, k_y)$:

$$f(k_x, k_y) = f_{mov}(k_x, k_y) \cdot e^{-\frac{2\pi i}{N} \cdot k_x \cdot k_y \cdot \Delta 1_x} \cdot e^{-\frac{2\pi i}{N} \cdot k_y^2 \cdot \Delta 1_y}$$

This can be followed by a standard image reconstruction with a multi-dimensional Fourier transformation.

The above comments for step 20 for the simple motion model of a linear motion can be correspondingly applied for more complex motion models. Thus, for example, a complex motion can be presented by a Taylor series or a sum of harmonics or the like, whereby the unknowns $\Delta I_x$ and $\Delta I_y$ are then to be considered functions. The time-dependency of the motion can thereby, for example, again be described by the k-space coordinate $k_y$, so that the following is valid for a direction of the motion model, for example according to a Taylor series, with the unknowns a, b and c:

$$\Delta l_x(a, b, c, k_y) = a + b \cdot k_y + c \cdot k_y^2$$

Only a signal-to-noise ratio of the values $f_{mov}(k_x, k_y)$ of the k-space matrix is considered as a limiting factor in the determination of motion models of different complexity according to the step 30.

That described above relating to FIGS. 1 through 3 can be correspondingly applied to sequences with a 3D acquisition and to three-dimensional k-space matrices generated therewith. An additional k-space coordinate $k_z$ merely has to be taken into consideration, and the motion model must be correspondingly designed three-dimensionally.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a magnetic resonance apparatus comprising the steps of:

obtaining a dataset as a plurality of complex number values from an image region of an examination subject disposed in an imaging volume of a magnetic resonance imaging apparatus, at least said image region being subject to motion, and entering said complex number values into respective locations in a k-space matrix;

generating a motion model identifying translational motion relative to said imaging volume with a time-dependency at least for selected points in said image region while obtaining said dataset;

generating said motion model with phase values of at least two of said complex number values of said k-space matrix that are point-symmetrically located in said k-space matrix relative to a symmetry point of said k-space matrix, said at least two complex number values being complex conjugates of each other in an absence of motion and having respectively different phase values dependent on said translational motion; and correcting said complex number values in said k-space matrix using said motion model.

2. A method as claimed in claim 1 comprising generating said motion model using a fit technique which minimizes a square of any error.

3. A method as claimed in claim 1 wherein the step of obtaining said dataset comprises obtaining said complex number values at respective registration times, and wherein the step of generating a motion model with a time dependency comprises generating said motion model with said time dependency defined by said registration times.

4. A method as claimed in claim 1 wherein said complex number values have respective coordinates in said k-space matrix, and wherein the step of generating a motion model with a time dependency comprises generating said motion model with said time dependency defined by at least one characteristic of said coordinates.

5. A method as claimed in claim 1 comprising generating said motion model to describe linear motion of said subject relative to said image region.

6. A method as claimed in claim 1 comprising generating said motion model as a Taylor series.

7. A method as claimed in claim 1 comprising generating said motion model as a sum of harmonics.

8. A method as claimed in claim 1 wherein the step of obtaining said dataset includes the steps of producing multiple radio-frequency excitations of said examination subject in said image volume, and obtaining the respective complex number values at respective registration times, and wherein the step of generating said motion model includes the step of omitting motion of said examination subject relative to said imaging volume which is identified as being allocated to a single one of said radio-frequency excitations.

9. A method as claimed in claim 1 comprising employing a slice technique for obtaining said dataset.

10. A method as claimed in claim 1 comprising employing a volume technique for obtaining said dataset.

* * * * *